United States Patent [19]
Pendleton et al.

[11] Patent Number: 4,849,416
[45] Date of Patent: Jul. 18, 1989

[54] TREATMENT OF CONDITIONS REQUIRING ENHANCED OXYGEN AVAILABILITY TO MAMMALIAN TISSUES

[75] Inventors: Robert G. Pendleton, Hatfield; Charles E. Pendley, II, Abington; John T. Suh, Maple Glen; Kin T. Yu, Collegeville; Paul R. Menard, North Wales; Tihamer Herczeg, Perkiomenville, all of Pa.

[73] Assignee: Rorer Pharmaceutical Corporation, Fort Washington, Pa.

[21] Appl. No.: 223,585

[22] Filed: Jul. 25, 1988

[51] Int. Cl.⁴ .............................. A61K 31/655
[52] U.S. Cl. ..................... 514/150; 514/814; 514/866; 514/921
[58] Field of Search .......................... 514/150

[56] References Cited

U.S. PATENT DOCUMENTS 2,396,145  3/1946  Askelof et al. ............... 534/664
4,626,431 12/1986  Batchelor et al. ............. 424/101
4,626,432 12/1986  Hyde et al. .................. 424/101

FOREIGN PATENT DOCUMENTS 0093381  4/1983  European Pat. Off. .

OTHER PUBLICATIONS

Teisseire et al., "Long-Term Physiological Effects of Enhanced O₂ Release by Inositol Hexapahosphate-Loaded Erythrocytes"; Proc. Natl. Acad. Sci. USA, vol. 84, pp. 6894–6898, Oct. 1987.

Pendleton et al., "Effect of Propranolol Upon the Hemoglobin-Oxygen Dissociation Curve", The Journal of Pharmacology and Experimental Therapeutics, vol. 180, No. 3, pp. 647–656, 1971.

Gross et al., "Effect of ortho-Iodo Sodium Benzoate on Hemoglobin-Oxygen Affinity in Normal and Ischemic Myocardium", The Journal of Pharmacology and Experimental Therapeutics, vol. 202, pp. 72–81, 1977.

Perutz et al., "Benzafibrate Lowers Oxygen Affinity of Haemoglobin", The Lancet, pp. 881–882.

Hyde, et al., "Modification of the Haemoglobin Oxygen Dissociation Curve in Whole Blood by a Compound with Dual Action", The Lancet, pp. 15–16, Jul. 1984.

Patterson et al., "Xanthone Additives for Blood Storage that Maintain its Potential for Oxygen Delivery", Transfusion, vol. 28, No. 1, pp. 34–37, 1988.

*Primary Examiner*—Douglas W. Robinson
*Assistant Examiner*—Raymond J. Henley, III

[57] ABSTRACT

Disclosed are pharmaceutical compositions containing certain heterocylcic sulphonamido azo compounds for enhancing oxygen availability to mammalian tissue.

21 Claims, No Drawings

TREATMENT OF CONDITIONS REQUIRING ENHANCED OXYGEN AVAILABILITY TO MAMMALIAN TISSUES

BACKGROUND OF THE INVENTION

1. Field of the Invention

This invention relates to a method of enhancing oxygen availability to mammalian, especially human, tissue. More particularly, the invention relates to modifying the affinity of hemoglobin for oxygen and thereby effecting adequate supply of oxygen to human tissue necessary for metabolism.

Certain clinical conditions are associated with increased demand for oxygen, namely, respiratory distress syndrome, shock, low cardiac output, heart and lung diseases, anemia, hyperthyroidism, cirrhosis of the liver, exercise, high altitude climbing and the like. Under these conditions it is desirable, and sometimes of life-saving necessity, to effect higher oxygen availability to the patient than is normally available. The present invention addressed methods and compositions to that end.

Blood circulating through the heart, arteries, veins and capillaries is vital to the functioning of the body, inter alia, for carrying nutriment and oxygen to the body cells and carbon dioxide back through the systemic veins for gas-exchange in the lungs. Blood consists of plasma containing the red blood corpuscles or erythrocytes, the while blood corpuscles or leukocytes, and blood platelets or thrombocytes. The oxygen transport system in man is the erythrocyte which contains the iron-protein conjugate, called hemoglobin. While the supply of oxygen to the cell is influenced by many factors, such as, the content and partial pressure of oxygen in the inhaled air, cardiac output and blood volume, the passive diffusion of oxygen from the lungs and its release to the tissues is mainly controlled by the affiinity of hemoglobin for oxygen.

This affinity is expressed by an oxygen hemoglobin dissociation curve having oxygen tension denoted by mm Hg, and oxygen saturation denoted by percentage as the coordinates. At 50% oxygen saturation ($P_{50}$) the oxygen tension is 27 mm Hg. An increase in blood acidity, carbon dioxide content, ionic concentration or temperature is known to shift the oxygen-hemoglobin equilibrium curve to the right by reducing hemoglobin affinity for oxygen and thereby increasing oxygen availability to the tissues. On the other hand, an increase in alkalinity of blood and tissues as well as a decrease in body temperature is known to shift the equilibrium curve to the left, and therefore, decrease oxygen availability.

Affinity of hemoglobin for oxygen is regulated by the level of certain intracellular organic phosphates, notably, 2,3-diphosphoglyceric acid (hereinafter, 2,3-DPG). Thus, the equilibrium curve can be shifted from normal either to the left or to the right by changing the concentration of intracellular 2,3-DPG in the red blood cells. The synthesis of 2,3-DPG is catalyzed by the enzyme 2,3-diphosphoglycerate synthase, the stimulation of which results in the maintenance or accumulation of 2,3-DPG in red blood cells. The degradation of 2,3-DPG, on the other hand, is catalyzed by the enzyme 2,3-diphosphoglycerate phosphatase. The inhibition of this enzyme, similarly, would result in the maintenance and accumulation of 2,3-DPG in red blood cells, accompanied by the maintenance and increase of oxygen availability.

2. Description of the Prior Art

It has been recognized by the prior art that oxygen-hemoglobin affinity is mainly regulated by the level of 2,3-DPG in mammalian red blood cells. (See of example: Benesh et al., Intracellular organic phosphates as regulators of oxygen release by hemoglobin, Nature, London, 221: 618–622, 1969; Oski et al. The Interrelationship Between Red Blood Cell Metabolites, Hemoglobin, and the Oxygen-Equilibrium Curve, Progress in Hemotology 7: 33, 1971.) Clinical conditions associated with alterations of 2,3-DPG levels include adaptation to high altitude, anemia, cirrhosis of the liver, heart and lung diseases and hyperthyroidism. These relationships were investigated by, for example:

Keys et al., Respiratory properties of the artierial blood in normal man and with patients with disease of the liver. Position of the oxygen dissociation curve, J. Clin. Invest., 17:59, 1938;

Morse et al., The position of the oxygen dissociation curve of the blood in cyanotic congenital heart disease, J. Clin. Invest., 29:1098, 1950;

Edwards et al., Improved oxygen release: An adaptation of mature red cells to hypoxia, J. Clin. Invest. 47:1851–1857, 1968;

Gahlenbeck et al., Veraenderung der Saurstoffbindungskurven des Blutes by Hperthyreosen und nach Gabe von trijodthyronin bei Gesunden und bei Rateen. Klin. Wschr. 46:547, 1968;

Keys et al., The position of the oxygen dissociation curve of human blood at high altitude, Amer. J. Physiol 115:292, 1936. Under these conditions delivery of oxygen to the tissues is impaired and the body's natural responses are inadequate to correct the tissue hypoxia.

To relieve hypoxic conditions, pharmaceutically active compounds, which shift the oxygen-hemoglobin dissociation curve to the right, were proposed and shown to be effective using appropriate test procedures. (See U.S. Pat. Nos. 4,626,431, 4,626,432 and EPO 0 093 381.) In addition to in vivo application, the compounds were also proposed for use in vitro blood storage to prolong useful shelf-life thereof. As to the mechanism or pathway involved in accomplishing the desired result, the compounds are said to induce right-displacement of the oxygen-dissociation curve.

The prior art has also discovered that the synthesis and degradation of 2,3-DPG are catalyzed by two enzymatic activities known respectively as 2,3-diphosphoglycerate synthase and 2,3-diphosphoglycerate phosphatase. (See: Rose, Z. B., J. Biol. Chem. 243, 4810, 1968 and Rose et al., J. Biol. Chem. 245, 3232, 1970). Accordingly, the stimulation of 2,3-diphosphoglycerate synthase or the inhibition of 2,3-diphosophoglycerate phosphatase, or both, shall result in the maintenance or increase of 2,3-DPG levels in the red blood cells.

The present invention is drawn to the inhibition of 2,3-diphosphoglycerate phosphatase by the utilization of certain compounds found to be effective to accomplish said inhibition and thereby providing for the maintenance and/or accumulation of 2,3-DPG levels which, as shown by the prior art, control the dissociation of oxygen/ hemoglobin. The mechanism involved in the inhibition of 2,3-diphosphoglycerate phosphatase is believed to be as follows.

2,3-diphosphoglycerate phosphatase is activated by a number of cellular metabolites, such as 2-phosphoglycolate, chloride and phosphate ions. 2-Phosphoglycolate is by far the most potent activator enhancing the activity of 2,3-diphosphoglycerate phosphatase by about 1600 fold at optimal concentrations. Preventing or lowering the interaction of 2-phosphoglycolate with 2,3-diphosphoglycerate phosphatease affords an excellent mechanism to control the 2,3-DPG levels in the cells allowing utilization of inhibitors in low concentrations.

SUMMARY OF THE INVENTION

The present invention relates to certain heterocyclic sulphonamido azo compounds of formula I:

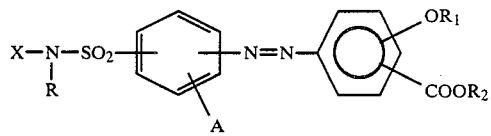

wherein

X is pyridyl, pheny, phenyl-substituted by lower alkyl, lower alkoxy, halogen, hydroxy, or nitro, furyl, pyrrolyl, quinolyl, pyrimidyl, thienyl or imidazolyl;

R, $R_1$ and $R_2$ are independently H, lower alkyl, lower aminoalkyl or

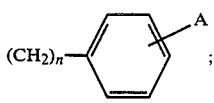

A is H, lower alkyl, lower aminoalkyl, amino, alkoxy, halo or $CF_3$;

n is 0 to 4; and, pharmaceutically acceptable salts thereof. Some of these compounds have been heretofore known for their bactericidal properties. U.S. Pat. No. 2,396,145 relates to such compounds and the same is incorporated herein by reference.

In the formula: pyridyl means 2-pyridyl, 3-pyridyl and 4-pyridyl; lower alkyl means alkyl having from one to six carbon atoms and includes straight-chained and branched groups; lower alkoxy means alkoxy having from one to six carbon atoms; halo means chloro, bromo, iodo, and fluoro groups; and amino means amino or an amino derivative such as $-NH_2$, $-NH-C(NH_2)-NH$ or

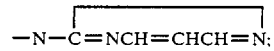

A particularly preferred compound is 5-[[p-(2-pyridylsulfamoyl)phenyl]azo]salicyclic acid or sulfasalazine known and used in the pharmaceutical industry as a potent anti-inflammatory drug, having the structure:

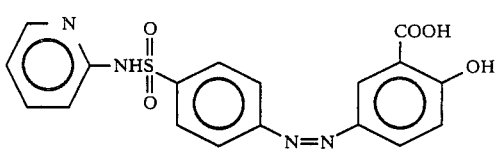

The pharmaceutically acceptable, non-toxic salts include salts of inorganic acids such as hydrochloric, hydrobromic, sulfuric and phosphoric, and of organic acids such as acetic, propionic, glycolic, lectic, malonic, succinic, malic, fumaric, tartaric, citric, ascorbic, benzoic, hydroxybenzoic, aminosalicyclic, cinnamic, mandelic, benzenesulfonic, toluenesulfonic, nicotinic, isonicotinic, and the like.

DETAILED DESCRIPTION OF THE INVENTION

The compounds of the present invention may be prepared by art-recognized methods from available starting materials, may also be prepared by the general procedure described in U.S. Pat. No. 2,396,145, or may be obtained from chemical supply houses, such as Aldrich Chem. Co.

The following synthetic scheme may be used to advantage in obtaining compounds used in the present invention.

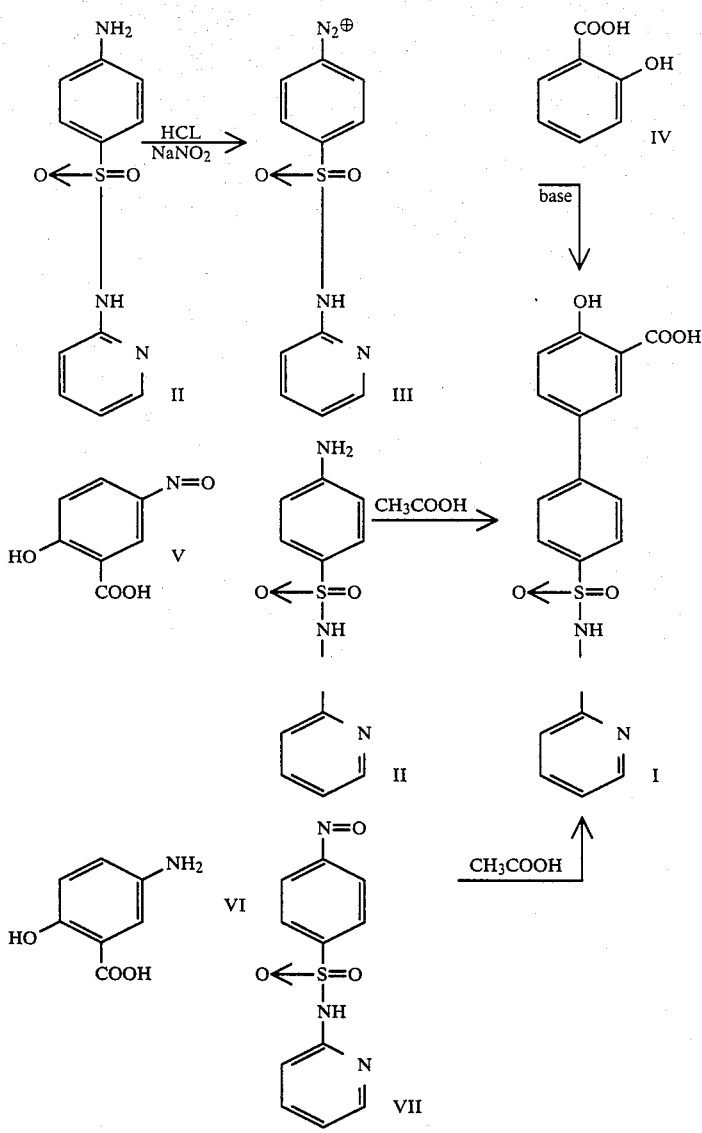

According to the synthetic scheme, sulfapyridine (compound II) is diazotized to produce the diazonium salt (compound III) which is then reacted with an alkaline solution of salicylic acid or an analog thereof (compound IV) to produce sulfasalazine (compound I) or analogs thereof.

Alternatively, 5-nitrososalicyclic acid (compound V) may be reacted with sulfapyridine (compound II) or analogs thereof; or, reacting nitroso-sulfapyridine (compound VII) with 5-amino-salicyclic acid (compound VI).

Other compounds encompassed by formula I, such as esters and ethers, may be prepared by reacting appropriately substituted salicyclic acid analogs and appropriately substituted sulfapyridine analogs. Alternatively, sulfasalazine analogs may be reacted with suitable esterifying or etherifying agents.

Representative examples for the preparation of compounds utilized in the present invention are shown in the before-cited U.S. Pat. No. 2,396,145.

The compounds of the present invention inhibit the activity of 2,3-diphosphoglycerate phosphatase which then results in the maintenance and accumulation of 2,3-DPG levels in red blood cells. The increase of 2,3-DPG displaces in vitro the oxygen-dissociation curve to the right of normal in whole human blood. Thus, the compounds are useful to provide a more effective delivery of oxygen to the tissues of mammals under certain circumstances and conditions when tissue hypoxia occurs. The prior art is cognizant of such conditions which includes anemia, trauma and shock, heart and lung diseases, diabetes, conditions associated with increased oxygen demand such as strenuous exercise, mountain climbing and the like, and certain surgical procedures.

The compounds may also be used in vitro both to maintain the oxygen delivery capacity of red blood cells and to extend shelf-life of transfusable blood on storage.

FORM AND DOSAGE OF ADMINISTRATION

According to the invention, the disclosed compounds may be utilized for effective delivery of oxygen to tissues in a mammal. For administration to a recipient, one or more compounds are formulated in compositions such as tablets, capsules or elixirs for oral administration or in sterile solutions or suspensions for parenteral administration. About 28 to 56,000 mg of a compound or mixture of compounds above-disclosed or physiologically acceptable salts(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage is in the range of from 0.4 mg/kg to 800 mg/kg body weight of the patient per day, more preferably in the range of from 4.0 mg/kg to 400 mg/kg of body weight per day, and most preferably in the range of from 10 mg/kg to 160 mg/kg of body weight.

A single dose, or preferably two to four divided daily doses, provided on a basis of about 0.2 to 400 mg/kg per day, preferably about 2 to 200 mg/kg per day is appropriate. The substance is preferably admininstered orally, but a parenteral route such as subcutaneously, intramuscularly, intravenously or intraperitoneally can also be employed.

Illustrative of the adjuvenants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservative, antioxidants and the like can be incorporated as required.

When used for extracorporeal treatment and in vitro storage of red blood cells, an effective blood concentration of a compound according to the invention will generally be in the range of from 0.001 mM to 10 mM, more preferably in the range of from 0.01 mM to 5 mM, and most preferably from 0.025 mM to 2 mM.

The method of introducing a composition of the invention into the blood for extracorporeal treatment is analogous to the technique used in hemodialysis wherey blood is withdrawn from the patient, admixed with a composition and passed back to the patient. The blood, of course, may also be treated batch by batch as necessary prior to transfusion. For storage, the blood is admixed with the composition in the collection vessel and transferred to appropriate storage containers using sterile techniques and storage conditions employed in the art.

METHODS OF TESTING 1. 2,3-Diphosphoglycerate Phosphatase Assay

The activity of 2,3-DPG phosphatase was determined radiochemically using a method based on Rose et al., (J. Biol. Chem. 245, 3232-3241, 1970). In this method the activity of the phosphatase is measured by determining the release of inorganic phosphate from the substrate, 2,3-DPG. The test compounds were dissolved in dimethyl sulfoxide at 100 times the final concentration used and then added to the reaction mixture at the beginning of the assay period. In the control experiments equivalent concentration of dimethyl sulfoxide was used.

14 $\mu$g of 2,3-DPG phosphatase was incubated in 0.2 ml of N-tris-[Hydroxy-methyl]methyl-2-aminoethanesulfonic acid [TES], at pH 7.5, containing 110 $\mu$M $^{32}$p-labeled 2,3-DPG (having a specific activity of 70 to 200 $\mu$Ci/$\mu$mol), 5 $\mu$M phosphoglycolate and 5 $\mu$M mercaptoethanol at 37° C. for 20 minutes in the presence and absence of the test compound. at the end of incubation the reaction was stopped by the addition of 0.1 ml of 15% w/v trichloroacetic acid and the sample was centrifuged (Eppendorf microfuge, Model 5413) in order to remove protein preciptitates. Then 0.2 ml of the supernatant was withdrawn and mixed with 0.1 ml of 8 M sulfuric acid, 0.1 ml of 5% w/v ammonium molybdate and 0.6 ml of water. The mixture then was extracted with 2 ml of isobutanol/benzene (1:1,v/v) and then centrifuged to effect separation of the phases. 1 ml of the organic phase containing the extracted $^{32}$p-phosphate was counted in a scintillation counter (Beckman, Model LS 8,000) using a program for $^{32}$p radioactivity. The activity of the enzyme was expressed as number of mole phosphate released per minute.

2. Determination of 2,3-Diphosphoglyceric Acid Content in Human Red Blood Cells

Blood samples from healthy subjects were collected in heparnized tubes and were centrifuged for 10 minutes at 400 xg. The plasma and buffy layer containing while cells and platelets was removed. The red blood cells were washed three times in Krebs Ringer Bicarbonate buffer supplemented with 2.5 mg/ml bovine serum albumin. The washed cells were suspended in the same buffer in a ratio of 1 cell to 4 buffer v/v. The cell suspension was incubated in siliconized glass beakers in the absence and presence of the test compound at 37° C. in air, supplemented with 5% v/v carbon dioxide. After incubation, 1 ml of the blood sample was mixed with 1 ml of 12% w/v trichloroacetic acid. The mixture was left at 4° C. for 10 minutes and then was clarified by centrifugation. The 2,3-DPG content in the supernatant was quantified using a Sigma assay kit based on the method described by Lowry et al, J. Biol. Chem. 239, 18, 1964.

From the data obtained using the radiochemical method, percent inhibition of 2,3-DPG phosphatase was calculated. Percent inhibition was found to be dose dependent, and it represents the magnitude of decrease in enzymatic activity relative to that measured in the absence of an active compound, i.e., relative to a control. Representative inhibitory activity is shown for sulfasalazine in Table I.

TABLE I

| Dose dependent inhibition of 2,3-DPG phosphatase by sulfasalazine | |
|---|---|
| Sulfasalazine Concentration ($\mu$M) | % Inhibition |
| 0 | 0 |
| 20 | 23 |
| 100 | 57 |

TABLE I-continued

| Dose dependent inhibition of 2,3-DPG phosphatase by sulfasalazine | |
|---|---|
| Sulfasalazine Concentration (μM) | % Inhibition |
| 500 | 86 |
| 1000 | 90 |

Inhibition of 2,3-diphosphoglyceric acid degradation in human red blood cells was also conducted on compounds of the present invention and is shown in Table II for sulfasalazine.

TABLE II

| Inhibition of 2,3-diphosphoglyceric acid degredation in human red blood cells by sulfasalazine | | | |
|---|---|---|---|
| | Sulfasalazine concentration (mM) | | |
| | 0 | 0.5 | 1.0 |
| Incubation period (hrs.) | 2,3-diphosphoglyceric acid content (μmole/ml RBC) | | |
| 0 | 4.4 | 4.4 | 4.4 |
| 3 | 3.7 | 3.9 | 4.1 |
| 6 | 2.4 | 3.0 | 3.5 |

While the invention in a method to enhance oxygen availability to mammalian tissue and to maintain the increase of 2,3-DPG levels in red blood cells has been described in detail, it will be recognized by those skilled in the art that considerable variation can be made in such detail without departing from the spirit of the invention as claimed.

What is claimed is:

1. A method of enhancing oxygen availability to the tissues in a mammal in need thereof comprising the administration of an effective oxygen availability enhancing amount of a compound of the formula:

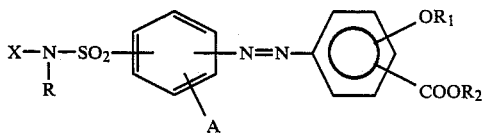

wherein
X is:
  pyridyl,
  phenyl,
  phenyl-substituted by lower alkyl, lower alkoxy, halogen, hydroxy, or nitro;
  furyl,
  pyrrolyl,
  quinolyl,
  pyrimidyl,
  thienyl or
  imidazolyl;
R, $R_1$ and $R_2$ are independently:
  H,
  lower alkyl,
  lower aminoalkyl,
  or

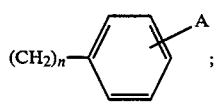

A is:
  H,
  lower alkyl,
  lower aminoalkyl,
  amino,
  alkoxy,
  halo, or
  $CF_3$;
n is:
  0 to 4; and
pharmaceutically acceptable salts thereof admixed with a pharmaceutically acceptable carrier.

2. The method of claim 1 wherein: R, $R_1$ and $R_2$ are H; and A is H.

3. The method of claim 1 wherein:
X is 2-pyridyl.

4. The method of claim 1 wherein:
X is 2-pyridyl;
$R_1$ is H;
A is aminoalkyl; and
$R_2$ is H.

5. The method of claim 1 wherein said compound is 5-[[p-(2-pyridylsulfamoyl)phenyl]azo]salicylic acid.

6. The method of claim 1 wherein said administration is oral.

7. The method of claim 1 wherein said administration is parenteral.

8. A method to relieve hypoxia in a mammal in need thereof comprising the administration to said mammal an effective hypoxia-relieving amount of a compound of the formula

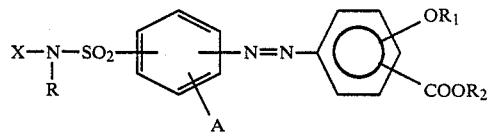

wherein
X is:
  pyridyl,
  phenyl,
  phenyl-substituted by lower alkyl, lower alkoxy, halogen, hydroxy, or nitro;
  furyl,
  pyrrolyl,
  quinolyl,
  pyrimidyl.
  thienyl or
  imidazolyl;
R, $R_1$ or $R_2$ are independently:
  H,
  loweralkyl,
  lower aminoalkyl, or

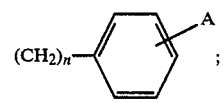

A is:
  H,
  lower alkyl,
  lower aminoalkyl,
  amino,
  alkoxy, halo, or
CF$_3$;
n is:
0 to 4; and
pharmaceutically acceptable salts thereof admixed with a pharmaceutically acceptable carrier.

9. The method of claim 8 wherein:
R, R$_1$ and R$_2$ are H; and
A is H.

10. The method of claim 8 wherein:
X is 2-pyridyl.

11. The method of claim 8 wherein:
X is 2-pyridyl;
R$_1$ is H;
A is aminoalkyl; and
R$_2$ is H.

12. The method of claim 8 wherein said compound is 5-[[p-(2-pyridylsulfamoyl)phenyl]azo]salicylic acid.

13. The method of claim 8 wherein said administration is oral.

14. The method of claim 8 wherein said administration is parenteral.

15. The method of claim 8 wherein said pharmaceutically acceptable carrier is in the form of a tablet.

16. The method of claim 8 wherein said pharmaceutically acceptable carrier is in the form of a capsule.

17. The method of claim 8 wherein said pharmaceutically acceptable carrier is in the form of an elixir.

18. The method of claim 8 wherein said pharmaceutically acceptable carrier is in the form of a sterile solution.

19. A method of maintaining oxygen delivery capacity of transfusable blood cells comprising admixing said blood prior to transfusion with an effective oxygen maintaining amount of a compound of the formula:

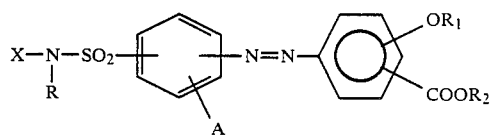

wherein
X is:
pyridyl,
phenyl,
phenyl-substituted by lower alkyl, lower alkoxy, halogen, hydroxy, or nitro;
furyl,
pyrrolyl,
quinolyl,
pyrimidyl,
thienyl or
imidazolyl;
R, R$_1$ or R$_2$ are independently:
H,
lower alkyl,
lower aminoalkyl, or

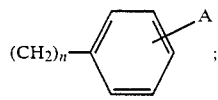

A is:
H,
lower alkyl,
lower aminoalkyl,
amino,
alkoxy,
halo, or
CF$_3$;
n is:
0 to 4; and
pharmaceutically acceptable salts thereof admixed with a pharmaceutically acceptable carrier.

20. The method of claim 19 wherein said transfusable blood cells are human blood cells.

21. A method of extending the shelf-life of transfusable red blood cells comprising admixing said red blood cells with a shelf-life extending effective amount of a compound of the formula:

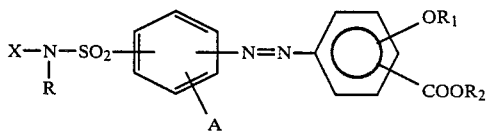

wherein
X is:
pyridyl,
phenyl,
phenyl-substituted by lower alkyl, lower alkoxy, halogen, hydroxy, or nitro;
furyl,
pyrrolyl,
quinolyl,
pyrimidyl,
thienyl or
imidazolyl;
R, R$_1$ and R$_2$ are independently:
H,
lower alkyl,
lower aminoalkyl, or

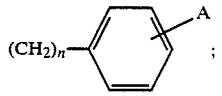

A is:
H,
lower alkyl,
lower aminoalkyl,
amino,
alkoxy,
halo, or
CF$_3$;
n is:
0 to 4; and
pharmaceutically acceptable salts thereof admixed with a pharmaceutically acceptable carrier.

* * * * *